United States Patent [19]
O'Connor et al.

[11] Patent Number: 5,893,875
[45] Date of Patent: Apr. 13, 1999

[54] SURGICAL INSTRUMENT WITH REPLACEABLE JAW ASSEMBLY

[75] Inventors: Paul D. O'Connor, East Bridgewater, Mass.; Christopher M. Batchelder, Wells, Me.; Giuseppe Lombardo, Bridgewater, Mass.

[73] Assignee: TNCO, Inc., Whitman, Mass.

[21] Appl. No.: 08/856,938

[22] Filed: May 15, 1997

Related U.S. Application Data

[63] Continuation of application No. 08/320,476, Oct. 7, 1994, abandoned.

[51] Int. Cl.$^6$ .............................. A61B 17/28; A61B 17/32
[52] U.S. Cl. .............................. 606/205; 606/174; 606/167
[58] Field of Search .............................. 606/1, 106, 110, 606/113, 114, 127, 167–178, 205, 206–211, 138–145

[56] References Cited

U.S. PATENT DOCUMENTS

| | | | |
|---|---|---|---|
| 5,152,778 | 10/1992 | Babs, Jr. et al. | 606/174 |
| 5,290,294 | 3/1994 | Cox et al. | 606/113 |
| 5,304,203 | 4/1994 | El Mallawany | 606/207 |
| 5,308,358 | 5/1994 | Bond et al. | 606/207 |
| 5,342,379 | 8/1994 | Volinsky | 606/167 |
| 5,368,606 | 11/1994 | Marlow et al. | 606/174 |
| 5,496,334 | 3/1996 | Klundt et al. | 606/145 |
| 5,593,402 | 1/1997 | Patrick | 606/205 |

*Primary Examiner*—Glenn K. Dawson
*Attorney, Agent, or Firm*—Stephen Y. Chow; Jerry Cohen; Christine M. Kuta

[57] ABSTRACT

A detachable and replaceable end effector assembly. The detachable mechanism is made of standard end effectors attached to an actuating tip and pinned inside a yoke assembly. Replacement is made by pulling back a spring loaded radial lock 90, to disengage two rear tabs 51 on the outer tip 50. The yoke assembly is then rotated 90 degrees to disengage the rear yoke pin 9 from the tubular shaft 70. This rotation of 90 degrees also unlocks the T-bar 45 from the front "T" slot of the long actuator 80. The end effector or jaw assembly is then free to be pulled away from the remainder of the shaft. In addition there is a bayonet connection to hold the parts together and prevent accidental disconnection.

8 Claims, 7 Drawing Sheets

SURGICAL INSTRUMENT WITH REPLACEABLE JAW ASSEMBLY

This application is a continuation of application(s) Ser. No. 08/320,476 filed on Oct. 7, 1994, now abandoned.

FIELD OF THE INVENTION

The present invention relates to micro-instrumentation, i.e. articulating hand held instruments used in micro-surgery various types of surgical instruments, such as are used e.g. in endoscopic surgery, including e.g. as to endoscopy and other fields, forceps, graspers, needle holders, scissors and punches differentiated by their working tip designs but using a common handle and tubular shafts, varying in length and/or diameter. The instruments can comprise scissor-handle-actuators, so-called cigar handle linear or rotary activators, or other actuators, with push or pull force application design modes.

The following discussion of the invention focusses on instruments required for endoscopic usage (minimally invasive procedures) and more particularly punches, scissors and graspers used in micro-surgery, in laparoscopic surgical procedures, and to other surgical instruments and non-surgical instruments.

Recent generations of enhanced miniaturization of endoscopic instruments have encountered the structural limits of thin cross-sections of the end effectors. As the tip area of such instruments is reduced, the likelihood of wear and tear or breakage and/or the need to reduce applied force becomes evident. The high strength and toughness of advanced metal alloys have not overcome this problem. Therefore such instruments break or wear out from to time to and must be discarded, or replaced.

It is a principal object of the invention to provide micro-instruments of the classes described above which are easily replaced.

It is a further object of the present invention to provide micro-instruments of the classes described above with easy and secure replaceable end effectors which can be changed even during a surgical procedure.

SUMMARY OF THE INVENTION

The present invention provides a detachable and replaceable end effector assembly. The detachable mechanism is made of standard end effectors attached to an actuating tip and pinned inside a yoke assembly. Replacement is made by pulling back a spring loaded radial lock, to disengage two rear tabs on the yoke. The yoke assembly is then rotated 90 degrees to disengage the rear yoke pin from the tubular shaft. This rotation of 90 degrees also unlocks the rear tabs of the actuator tip from the front "T" slot of the actuating rod. The end effector or jaw assembly is then free to be pulled away from the remainder of the shaft.

Other objects, features and advantages will be apparent from the following detailed description of preferred embodiments taken in conjunction with the accompanying drawings in which:

2

DETAILED DESCRIPTION OF PREFERRED EMBODIMENTS

Figures 1, 2, 3:
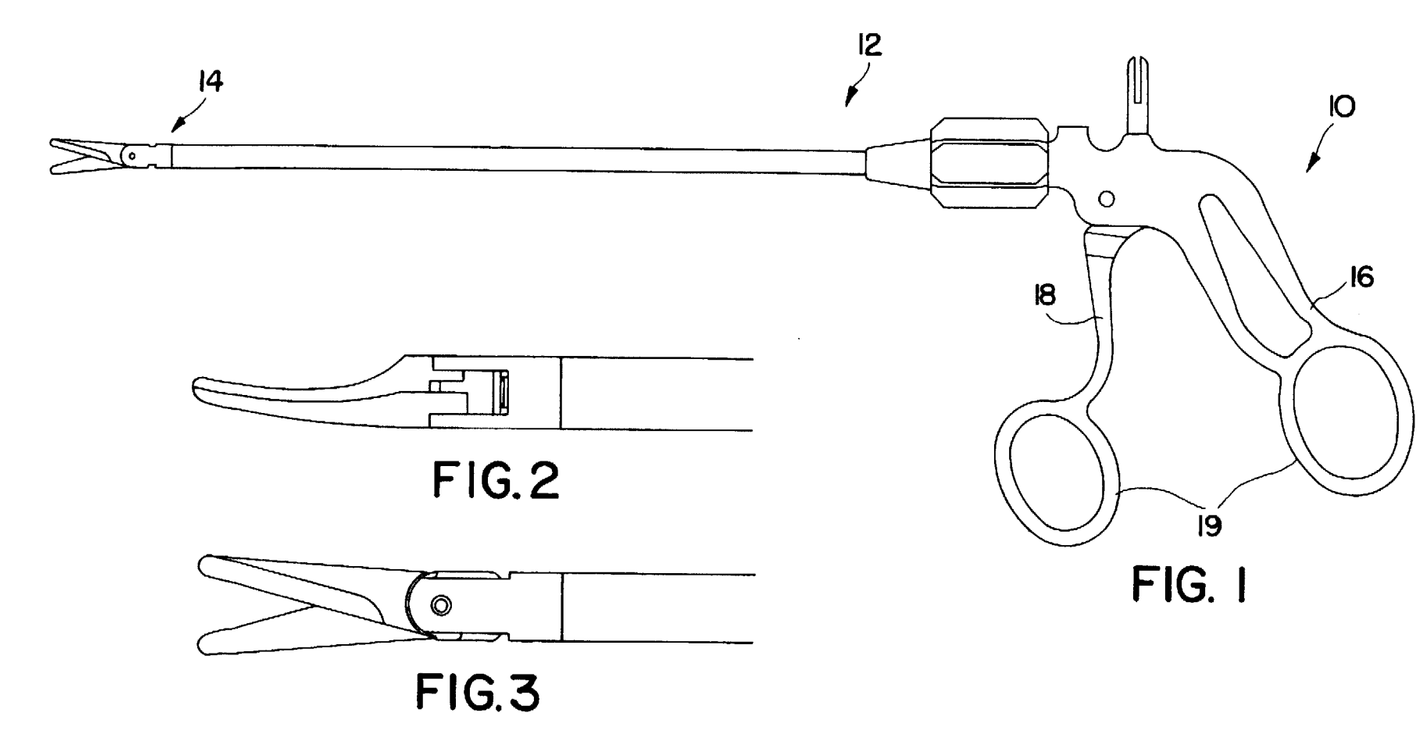
FIG. 1 is a side elevational view of a surgical instrument of the type to which the present invention belongs.
FIG. 2 is a top view of the effector end of the instrument.
FIG. 3 is a side view of the effector end of the instrument.

FIG. 1 shows a surgical device of the type which includes the present invention. It includes a handle assembly 10 of an articulating, hand-held instrument 12 having a distal articulating assembly or end effector 14 of a cutting type, such as that used in surgery, electronic assembly and like applications. In this case it is a surgical scissors. It includes a fixed handle section 16, and an articulating handle portion 18. The grasping elements 19 of the handle portions are of closed-loop design. FIGS. 2 and 3 show more details of the top and side, respectively, of the end effector scissors.

Figure 4:
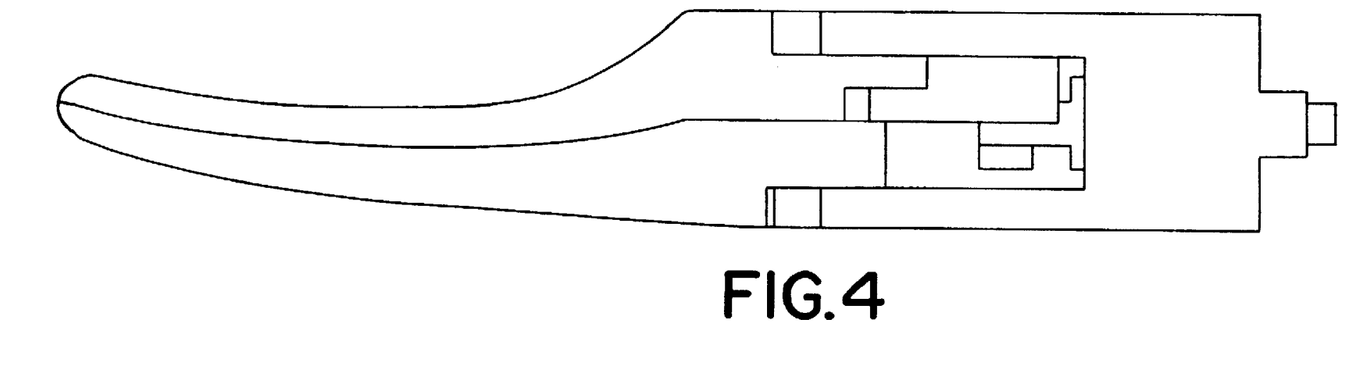
FIG. 4 is a sectional view of the effector end of the instrument.

An end effector of the scissors type is shown in FIG. 4, having an outer tip 50 which has two diametrically mounted tabs 51 projecting away from the effector end. The two holes in the outer tip are shown and will be discussed further below. Some of the internal parts which are not visible from FIG. 4 can be seen in FIG. 5 in which one of two actuator fronts 60 and the short actuator 40 can be seen.

Figure 6:
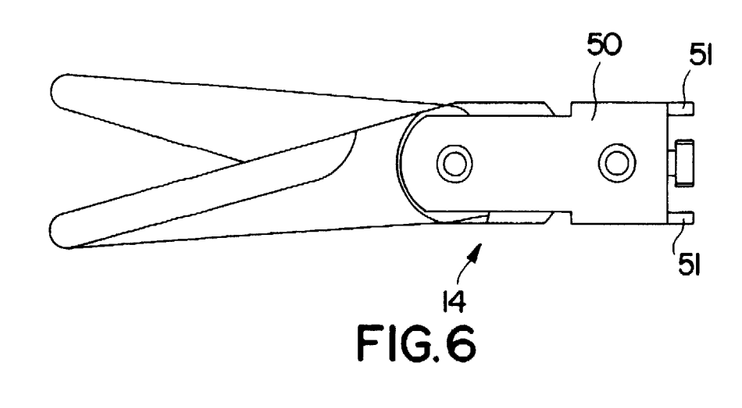
FIG. 6 is a sectional view similar to FIG. 4.
Figure 7:
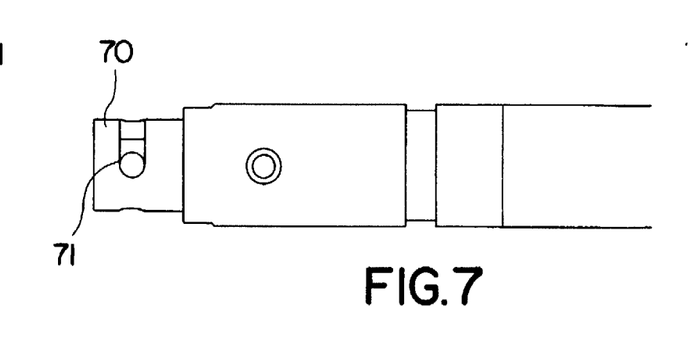
FIG. 7 is a sectional view showing the control and support end onto which the end effector is attached.
Figure 8:
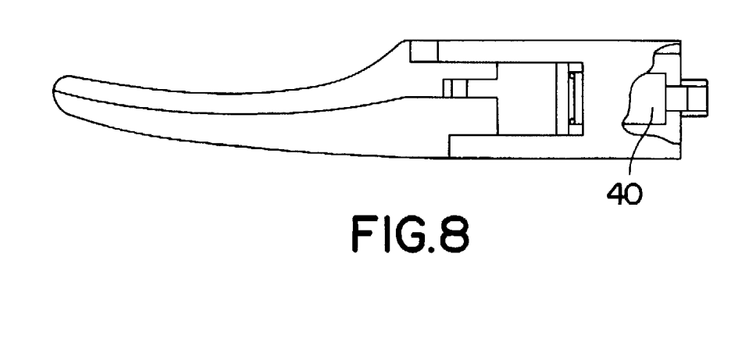
FIG. 8 is a partial sectional top view of the end effector.

FIG. 6 is a view similar to FIG. 4 but shows the end of the short actuator 40 projecting from the end effector. The outer tip 50 which acts as a yoke and its two diametrically mounted tabs 51 projecting away from the working end can be seen. The tabs 51 are for use in the attachment/detachment process and also to lock the parts from rotation when the parts are locked together to prevent accidental unlocking. Within the outer tip 50 are the two actuator fronts 60 which are mirror images of each other, and the short actuator 40, more details of which can be seen in FIG. 8 and FIGS. 10–12. The end of the permanent assembly includes a welded sleeve 70 being shown at the left end in FIG. 7, and a sliding sleeve 90 surrounds it.

Figure 5:
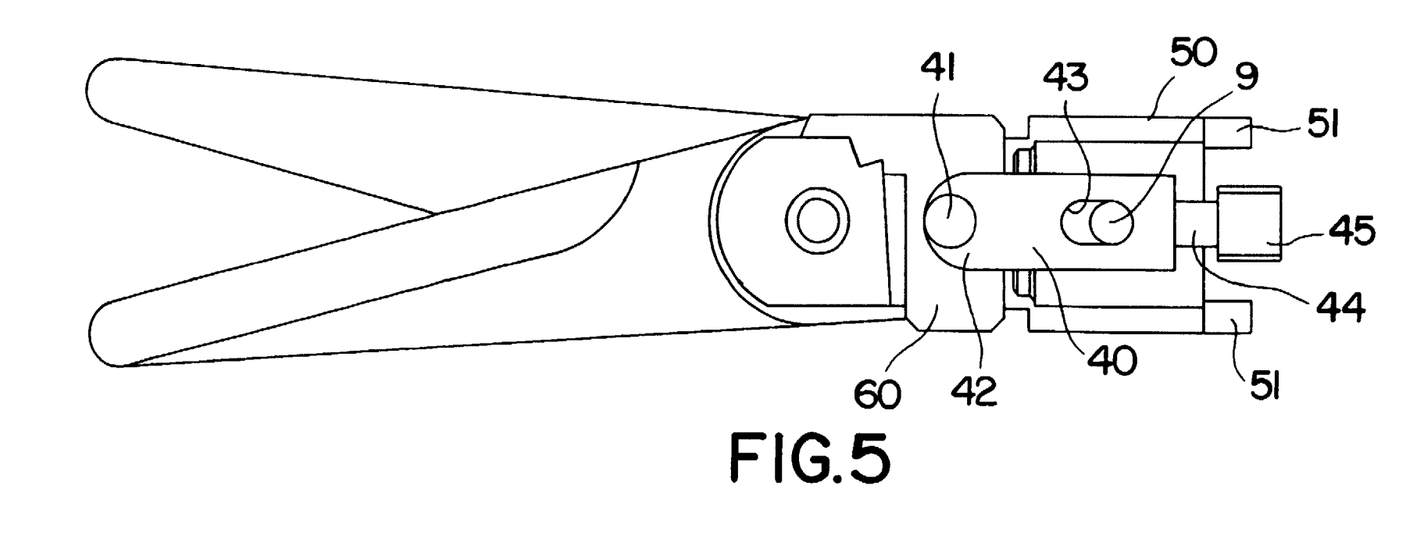
FIG. 5 is a further sectional view of the effector end of the instrument showing more of the internal parts.
Figure 20:
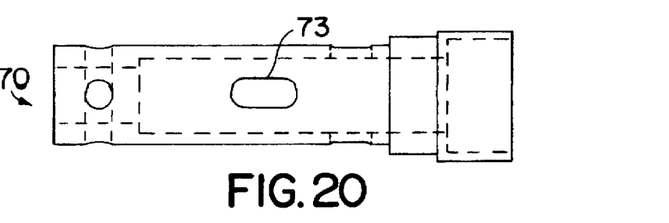
FIG. 20 is a side elevational view of the welded sleeve.
Figure 21:
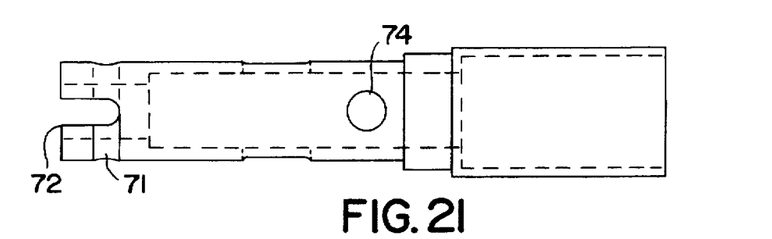
FIG. 21 is a top elevational view of the welded sleeve.
Figure 22:
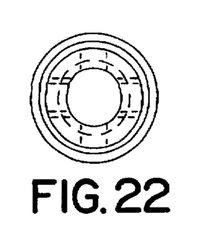
FIG. 22 is an end elevational view of the welded sleeve.

The welded sleeve, shown in detail in FIGS. 20–22, which includes a few cylindrical sections and which includes an opening 72, and a slot 73 as well as a hole 74. The sleeve also includes L-shaped bayonet slots 71 which accommodate the rear yoke pin 9 (FIG. 5).

Figure 9:
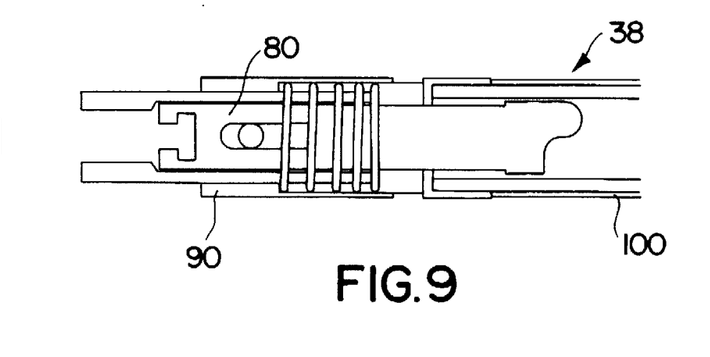
FIG. 9 is a sectional side view of the control and support end onto which the end effector is attached.

The internal parts of the control and support which is the permanent part of the assembly, the end effector being replaceable, include the control rod or tip outer shaft 100 shown within the assembly. There is a long actuator 80 disposed within the welded sleeve 70 as can be seen in FIG. 9.

Figure 23:
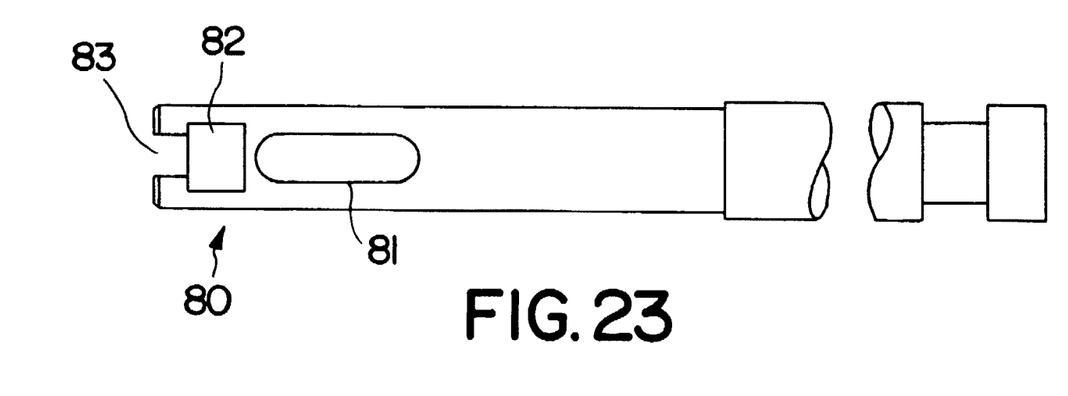
FIG. 23 is a side elevational view of the long actuator.
Figure 24:
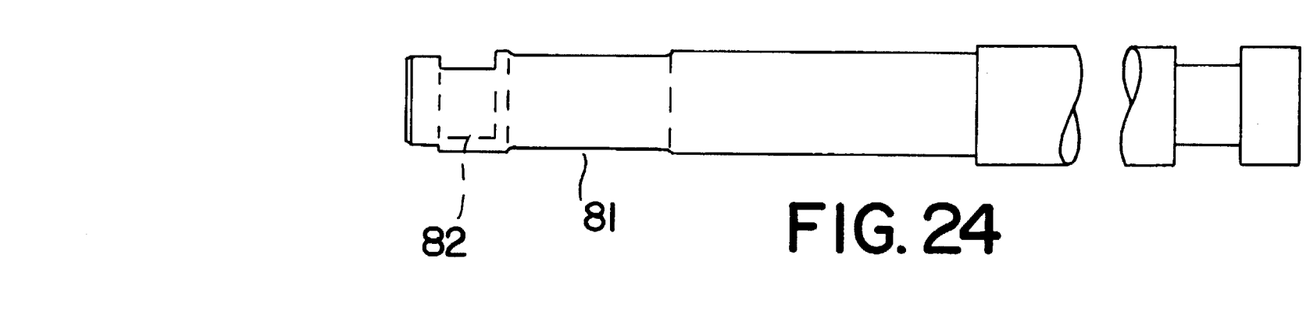
FIG. 24 is a top elevational view of the long actuator.
Figure 25:
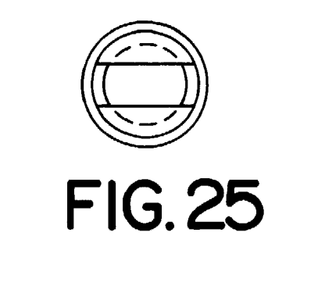
FIG. 25 is an end elevational view of the long actuator.

The long actuator is shown in more detail in FIGS. 23–25, and includes a cylindrical body having a slot 81, a T-slot 82, and an opening 83 in the end to allow a part to obtain access to the T-slot.

Figures 26, 28:
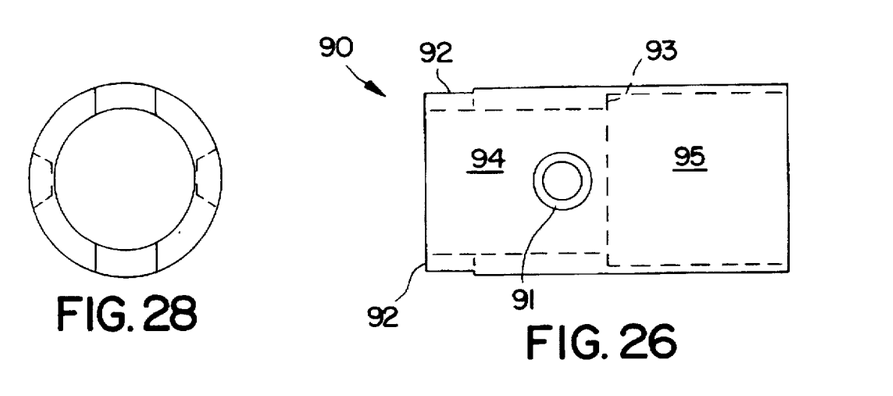
FIG. 26 is a side elevational view of the sliding sleeve.
FIG. 28 is an end elevational view of the sliding sleeve.
Figure 27:
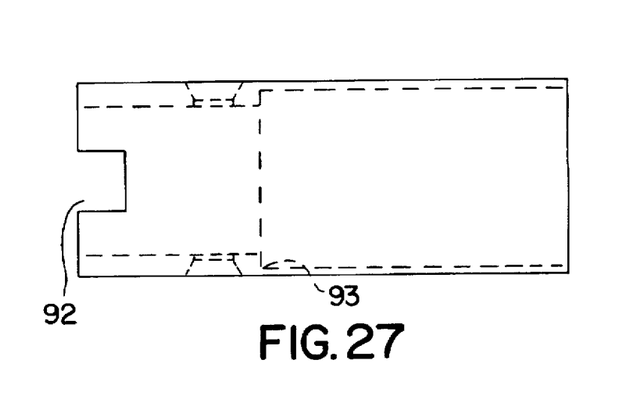
FIG. 27 is a top elevational view of the sliding sleeve.
Figure 29:
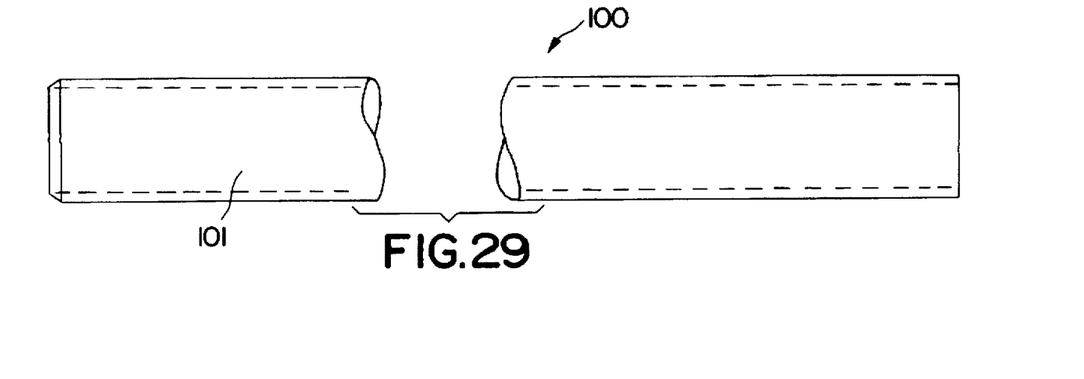
FIG. 29 is a side elevational view of the tip outer shaft shown broken in the middle.

The sliding sleeve is shown in detail in FIGS. 26–28, and is cylindrical with central openings passing therethrough. There is a hole 91, and slots 92 into which tabs 51 extend when the parts are locked together. There is a shoulder 93 formed at the area where the central openings are of two different diameters. The two central bores are denoted at 94 and 95.

Figure 10:
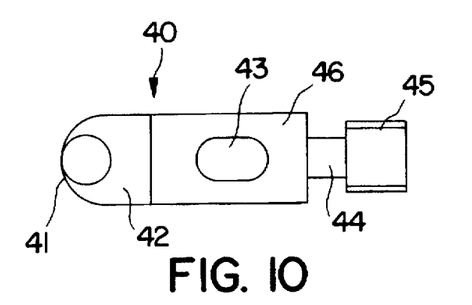
FIG. 10 is a side elevational view of the short actuator.
Figure 10A:
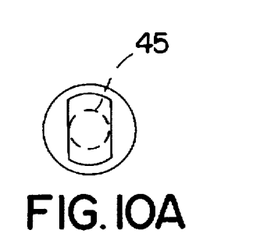
FIG. 10A is an end elevational view of the short actuator.
Figure 11:
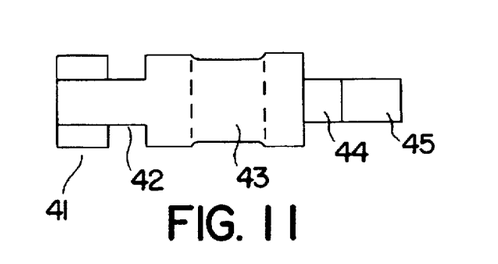
FIG. 11 is a top elevational view of the short actuator.
Figure 12:
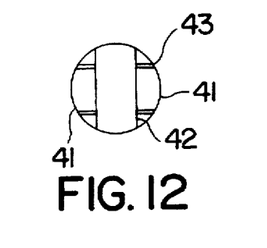
FIG. 12 is an end elevational view of the short actuator.
Figure 13:
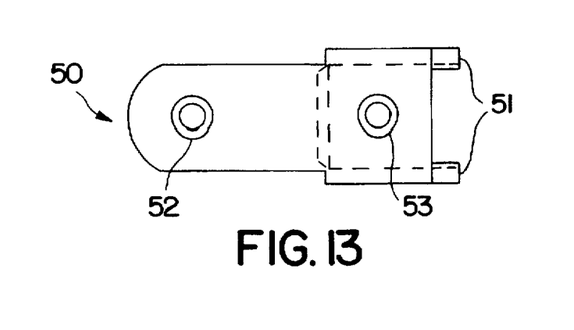
FIG. 13 is a side elevational view of the outer tip.
Figure 14:
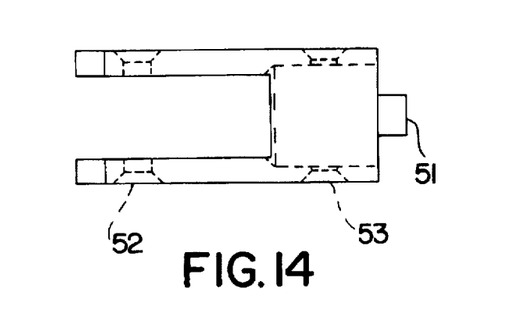
FIG. 14 is a top elevational view of the outer tip.
Figure 15:
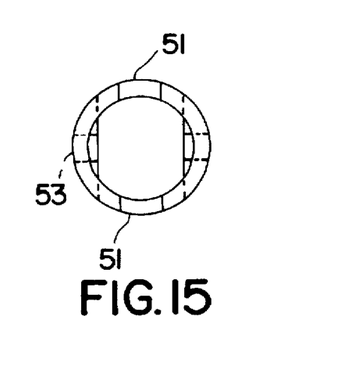
FIG. 15 is an end elevational view of the outer tip.
Figure 16:
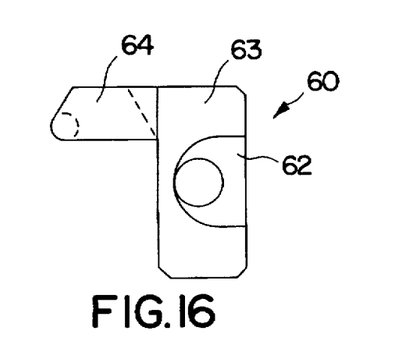
FIG. 16 is a side elevational view of the actuator front.
Figure 17:
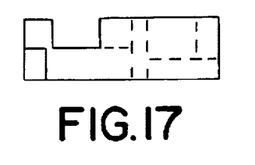
FIG. 17 is a top elevational view of the actuator front.
Figure 18:
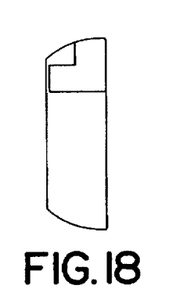
FIG. 18 is a left end elevational view of the actuator front.
Figure 19:
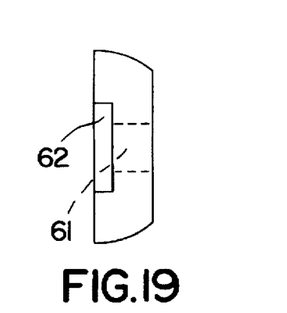
FIG. 19 is a right end elevational view of the actuator front.

The end effector which is detachable in accordance with the present invention, includes an outer tip 50 in which is located the short actuator 40 and the two actuator fronts 60. The outer tip 50 has a cylindrical portion and a pair of legs projecting therefrom. A hole 52 is formed in each leg. There is also a hole 53 in the cylindrical portion. There are tabs 51 which project from the cylindrical portion. The end effectors are pivotally mounted in the openings in the end of the outer tip at the end opposite the tabs 51. The short actuator 40 has a slot 43 in the cylindrical portion 46, a shaft 44 which projects from the control end, and a T-bar 45 which fits into the T-slot. The projecting pins 41 are on its portion 42, which, as shown in FIGS. 10–12, is flat along a longitudinal portion, and round at the effector end. This flat curved portion is attached to a cylindrical portion in which the slots 43 are located. These pins 41 fit into grooves in the pair of actuator fronts 60 at one end. The other ends of the actuator fronts 60 assist in movement of the end effectors when the T-tab end of the short actuator is moved which in turn moves the actuator fronts. The left end of the short actuator of FIG. 10 sits in the slot and groove of the actuator front as in FIG. 16. Each actuator front has a leg 63 in which is formed a groove 62 and an opening 61. There is also a shorter leg 64.

The permanent control and support section includes the tip outer shaft 100 having a central bore 101 therethrough within which is located the long actuator 80 which is the movable and thus the controlable element which is moved by movement of the scissors type handle to move the end effector blades. The left end of the long actuator has a T-slot into which the T-tab of the short actuator sits during operation. The welded sleeve fits over the end of the long actuator and has bayonet slots 71 which accomodates yoke pin 9 on either side of the short actuator 40 and inside outer tip or yoke 50 (as shown in rotated cross-section of the end effector in FIG. 5) to lock the parts together. The tabs 51 on the outer tip fit into slots in the sliding sleeve to prevent the outer tip and the sliding sleeve from rotating with respect to each other. This therefore prevents the bayonet connection from opening.

When it is desired to remove the end effector from the support and control section, the sliding sleeve 90 is moved to the right in FIG. 9 against the force of the spring, until the slots in the sliding sleeve are moved past the ends of the tabs 51 of the outer tip so that relative rotation can take place. Then, the parts are rotated so that yoke pin 9 is disengaged from bayonet slots 71, and the parts can be separated, and a new end effector can be attached, when it is worn, so that the entire instrument does not have to be replaced.

The unlocking rotation means there is 90 degree rotation to disengage the rear yoke pin 9 from the tubular shaft. This rotation of 90 degrees also unlocks the T-bar 45 from the front "T" slot of the long actuator 80. The end effector or jaw assembly 14 is then free to be pulled away from the remainder of the shaft.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A medical instrument with a replaceable distal end, comprising:
   a. a handle for actuating the instrument;
   b. a distal operating section for performing a medical procedure effected by a reciprocating action actuated by said handle;
   c. a middle section connecting said handle with said operating section and transmitting via a reciprocating actuating link said reciprocating action actuated by said handle;
   d. means removably connecting said distal operating section with said middle section for allowing said operating section to be replaced, said removably connecting means allowing removal without action of said handle by simultaneous disengagement from said middle section and said actuating link by a less-than-180-degree rotation relative to said middle section and said actuating link.

2. A medical instrument as defined in claim 1, wherein said operating section engages said actuating link by a T-tab which fits into a T-slot in said actuating link.

3. A medical instrument as defined in claim 1, wherein said operating section comprises a yoke which engages with a sliding member that is spring-loaded toward said operating section on said middle section and which is disengaged by sliding said sliding member away from said operating section.

4. A medical instrument as defined in claim 3, wherein the yoke comprises tabs which fit into slots in the sliding member.

5. A medical instrument as defined in claim 4, wherein the actuating link is restrained against rotational movement relative to the middle section.

6. A medical instrument as defined in claim 5, wherein said sliding member is restrained against rotational movement by a pin extending radially through the sliding member, which extends through a slot in the actuating link.

7. A medical instrument as defined in claim 3, wherein said operating section is removed by rotation of approximately 90 degrees relative to said middle section.

8. A medical instrument with a replaceable distal end, comprising:
   a. a handle for actuating the instrument;
   b. a distal operating section for performing a medical procedure effected by a reciprocating action actuated by said handle;

c. a middle section connecting said handle with said distal operating section and transmitting via a reciprocating actuating link said reciprocating action actuated by said handle;

d. means removably connecting said distal operating section with said middle section for allowing said distal operating section to be replaced, said removably connecting means comprising means for engaging said actuating link and said middle section by rotating said distal operating section relative to said middle section, defining a bayonet locking mechanism locked into place by a sliding member at the distal operating section end of said middle section.

* * * * *